United States Patent [19]
Powell et al.

[11] Patent Number: 5,456,906
[45] Date of Patent: Oct. 10, 1995

[54] ANTIPERSPIRANT COMPOSITIONS

[75] Inventors: Virginia V. Powell, East Nassau; Stanley J. Stoklosa, Clifton Park; Raymond J. Thimineur, Scotia, all of N.Y.

[73] Assignee: General Electric Company, Waterford, N.Y.

[21] Appl. No.: 154,246

[22] Filed: Nov. 17, 1993

[51] Int. Cl.$^6$ .............................. A61K 7/34; A61K 7/38; A61K 9/10
[52] U.S. Cl. ............................ 424/66; 424/68; 514/938; 514/944
[58] Field of Search .......................................... 424/66, 68

[56] References Cited

U.S. PATENT DOCUMENTS

| | | | |
|---|---|---|---|
| 4,954,333 | 9/1990 | Ward | 424/66 |
| 4,980,156 | 12/1990 | Raleigh et al. | 424/66 |
| 5,008,103 | 4/1991 | Raleigh et al. | 424/66 |
| 5,160,732 | 11/1992 | Katsoulis et al. | 424/47 |
| 5,162,378 | 11/1992 | Guthauser | 424/66 |
| 5,194,249 | 3/1993 | Drucker et al. | 424/66 |
| 5,216,033 | 6/1993 | Pereira et al. | 424/66 |
| 5,225,188 | 7/1993 | Abrutyn et al. | 424/68 |
| 5,232,689 | 8/1993 | Katsoulis et al. | 424/66 |
| 5,271,934 | 12/1993 | Goldberg et al. | 424/47 |

*Primary Examiner*—Dale R. Ore

[57] ABSTRACT

The present invention provides novel water-in-oil antiperspirant compositions which are transparent or substantially transparent, leave no white residue, and have a non-tacky feel.

21 Claims, No Drawings

ANTIPERSPIRANT COMPOSITIONS

The present invention relates to clear antiperspirant (AP) compositions. More particularly the present invention relates to clear, non-tacky, non-whitening, water-in-oil antiperspirant compositions made from silicone terpolymers.

BACKGROUND OF THE PRESENT INVENTION

Silicone terpolymers, particularly long-chain alkyl modified polysiloxane-polyoxyalkylene copolymers are known to those of ordinary skill in the art and are discussed in the literature, for example, see U.S. Pat. No. 4,980,156 to Raleigh et al. relating to non-transparent antiperspirant compositions.

It has now been found that novel AP compositions where the different phases have essentially the same refractive indices that result in clear, non-whitening antiperspirant emulsions. By clear it is meant the antiperspirant will be transparent or substantially transparent in a typical consumer application measuring approximately 1" thick. In addition, these products will be non-whitening, leaving no visible residue on the skin.

SUMMARY OF THE INVENTION

According to the present invention there is provided an AP composition comprising a long-chain hydrocarbon-modified polydiorganosiloxane polyoxyalkylene copolymer containing polydimethylsiloxy groups, on average at least one long-chain alkyl (methyl) siloxy group, and on average at least one polyoxyalkylene group, having the general formula:

$$MD_xD'_yD''_zM$$

wherein

D is $(CH_3)_2SiO_{2/2}$;

D' is $(CH_3)R'SiO_{2/2}$, where R' is an alkyl group having from about 6 to about 30 carbon atoms;

D'' is $(CH_3)R^2SiO_{2/2}$ where $R^2$ is a polyoxyalkylene ether segment of the formula

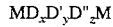

wherein each individual $R^3$ is a substituted or unsubstituted alkylene radical having 2 to 6 carbon atoms, $R^4$ is a substituted or unsubstituted alkylene radical having 2 to 20 carbon atoms, and $R^5$ is hydrogen or a substituted or unsubstituted hydrocarbon radical of from 1 to about 12 carbon atoms, and n has an average value from about 5 to about 20, p has a value of zero or 1, M is $(CH_3)_2R^6SiO_{2/2}$, where $R^6$ may be an alkyl group having from 1 to 30 carbon atoms or $R^2$;

x has an average value of from about 10 to about 400;

y has an average value of from 1 to about 200;

z has an average value of from 1 to about 100; and x+y+z has an average value of from about 12 to about 400;

a volatile liquid;

a solubilizing agent;

water;

a refractive index adjuster; and an astringent salt.

DETAILED DESCRIPTION OF THE PRESENT INVENTION

The long-chain hydrocarbon-modified polydiorganosiloxane polyoxyalkylene copolymer of the novel AP compositions of the present invention contains polydimethylsiloxy groups, on average at least one long-chain alkyl (methyl) siloxy group, and on average at least one polyoxyalkylene group, having the general formula:

$$MD_xD'_yD''_zM$$

wherein

D is $(CH_3)_2SiO_{2/2}$;

D' is $(CH_3)R'SiO_{2/2}$, where R' is an alkyl group having from about 6 to about 30 carbon atoms, preferably about 8 to about 18 carbon atoms, and most preferably about 10 to about 12 carbon atoms:

D'' is $(CH_3)R^2SiO_{2/2}$ where $R^2$ is a polyoxyalkylene ether segment of the formula

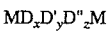

wherein each individual $R^3$ is a substituted or unsubstituted alkylene radical having 2 to 6 carbon atoms, $R^4$ is a substituted or unsubstituted alkylene radical having 2 to 20 carbon atoms, and $R^5$ is hydrogen or a substituted or unsubstituted hydrocarbon radical of from 1 to about 12 carbon atoms, and n has an average value from about 5 to about 20, p has a value of zero or 1, M is $(CH_3)_2R^6SiO_{2/2}$, where $R^6$ may be an alkyl group having from 1 to 30 carbon atoms or $R^2$;

x has an average value of from about 10 to about 400;

y has an average value of from 1 to about 200;

z has an average value of from 1 to about 100; and x+y+z has an average value of from about 12 to about 400, The polyoxyalkylene segments of the copolymer comprise oxyethylene units of the formula $—CH_2CH_2O—$, alone or in combination with oxyalkylene units of the formula $—C_nH_{2n}O—$, where n has a value of 3 to about 6, an average of at least half of the oxyalkylene units of the polyoxyalkylene segments being oxyethylene units. Suitable emulsions of this invention are not formed when the polyoxyalkylene segments contain more than 50 mol percent of the relatively hydrophobic higher oxyalkylene units. The polyoxyalkylene segments thus correspond to the formula $(—CH_2CH_2O—)_r$, $(C_nH_{2n}O)_q$ wherein the oxyalkylene units may be arranged in any suitable fashion such as random, alternating and block. The average values of r and q are such that r is $\geq q$ and the sum r+q=n, where n has an average value of from about 5 to about 20 as stated above. The preferred polyoxyalkylene segments consist solely of oxyethylene units. It is critical herein that the number of repeating units of $—OR_3—$, i.e. the value of n, be between about 5 and 20. Thus, in the case of ethylene oxide as the repeating unit, the molecular weight of $R^2$ should be less than about 900. The preferred value of n is from 10 to 15, which for ethylene oxide provides a molecular weight for $R^2$ of no more than about 700. $R^4$ is the group which bonds the polyoxyalkylene segment to the polysiloxane. $R^4$ may be $—CH_2CH_2CH_2—$, $—CH_2CH_2—$, $—CH=CH—CH_2—$, $—CH_2CH_2CH_2CH_2—$, etc. Preferably, R4 is $—CH_2CH_2CH_2—$. When p is zero the segments are joined by $—O—$ which is the product of a condensation reaction between a condensable end group on polyalkylene oxide. Although the copolymer is not soluble in water and therefore is not subjected to vigorous hydrolysis conditions in the compositions of this invention, it is preferred that p be 1, avoiding the use of the hydrolyzable carbon-oxygen-silicon bond to link the polyoxyalkylene segment to the polysiloxane chain.

$R^5$ is the terminal group of the polyalkylene ether. The type of $R^5$ is not critical and may be selected from hydrogen, methyl, ethyl, propyl, butyl, phenyl, acetyl, etc. Preferably $R^5$ is hydrogen.

The radical $R^6$ of the end-blocking group M may be a lower alkyl group, or else an alkyl group derived from the olefin used to form the R' groups of the element $D^1$ or an $R^2$ group derived from the polyether used to form $R^2$ groups when the polysiloxane containing silicon hydride groups is end-blocked with dimethylhydrogen siloxy groups. It is preferred however to utilize a polysiloxane starting material which case $R^6$ is methyl.

The copolymers may be prepared by any suitable method; several are disclosed in the organosilicon art. A preferred method for preparing the polydiorganosiloxane component comprises reacting a methyl siloxane having terminal and/or in-chain silicon-bonded hydrogen atoms with an olefin having from 6 to 30 carbon atoms, such a 1-octene, 1-octadecene or -dodecene, and an olefinically terminated polyoxyalkylene, such as $CH_2=CHCH_2O(CH_2CH_2O)_p(C_nH_{2n}O)_qH$ in the presence of a platinum-containing catalyst, such as $H_2PtCl_6.H_2O$. In this preferred method the olefin and the olefinically terminated polyoxyalkylene are most preferably reacted sequentially, olefin first, with the methylsiloxane containing silicon-bonded hydrogen radicals. The disclosures of U.S. Pat. Nos. 3,657,305; 3,234,252, 4047,958; 3,427,271 and 2,846, 458 are hereby incorporated herein by reference to further show methods for preparing the polydiorganosiloxane component of the compositions of this invention. It is to be understood that polydiorganosiloxanes that have been prepared in this preferred manner can contain small amounts of unreacted olefin and/or olefin-terminated polyoxyalkalene.

The volatile liquid of the present invention is a fluid selected from methylsiloxane fluids or organic fluids having a normal, i.e. atmospheric pressure, boiling point of less than 250° C.

The volatile methylsiloxane fluid has the average unit formula

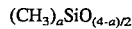

$$(CH_3)_aSiO_{(4-a)/2}$$

where a has an average value of from 2 to 3 and consists of siloxane units selected from the group consisting of $(CH_3)_3SiO_{1/2}(CH_3)SiO_{2/2}$, $CH_3SiO_{3/2}$ and $SiO_{4/2}$ units. Preferably, the volatile methylsiloxane fluid consists essentially of dimethylsiloxane units, and optionally, trimethylsiloxane units. Of particular value as volatile liquid are the cyclic siloxanes of the general formula $[(CH_3)_2SiO]_b$, and the linear siloxanes of the general formula $(CH_3)_3SiO[(CH_3)_2SiO]_cSi(CH_3)_3$, and their mixtures, wherein b is an integer of from 3 to 6 and c is an integer of from 0 to 4. A highly preferred methylsiloxane fluid is a mixture of said cyclic siloxanes wherein a major portion is tetramer (b=4) or (b=5).

Examples of organic fluids are isoparaffinic hydrocarbons, alcohols and esters. The amount of volatile liquid used is from about 5 to about 40 parts and preferably from about 10 to about 30 parts, and still more preferably from about 15 to about 20 parts.

Solubilizing agents are also contemplated for use in the present invention. These solubilizing agents can be organic oils or low viscosity silicone fluids, that are miscible or soluble in the compositions of the present invention. Specific solubilizing agents include isopropyl palmitate, isopropyl myristate, lauryl alcohol, and silicone fluids having a viscosity less than 50 cstks such as SF-96-5 offered by GE Silicones and product, with the CFTA name: Phenyl Trimethicone and the like. The amount of solubilizing agent present is from about 0.1 parts to about 20 parts of the total composition and preferably is from about 1.0 parts to about 10.0 parts.

Refractive Index (RI) adjusters are contemplated for use in the present invention. These RI adjusters include compounds for raising the RI value of the water-phase of the compositions as well as compounds RI of the phases.useful for lowing the RI of the oil-phase of the compositions. Such compounds include, propylene glycol, glycerin, sorbitol, silicone polyether copolymer or any water soluble-polar-type material. Water soluble inorganic salts, such as sodium chloride can also be used to adjust the water phase. In addition to the water based RI adjusters, oil phase adjusters such as esters, hydrocarbon oils such as mineral oil, long-chain alcohols or other mixtures can be used. The amount of RI adjuster used varies depending on the RI of the water- and oil- phases, and is generally present in an amount sufficient to adjust the RI of the water phase and oil phase to obtain optical clarity. This means the RI of the two phases are within at least about 0.0020 RI units of each other, and preferably within about 0.00010 units and most preferably there is no difference in Astringent salts can also be present in the compositions of the present invention. Examples of well-known astringents include aluminum, hafnium and zirconium salts, such as zirconyl hydroxide halides, aluminum zirconium chloride, zirconium-aluminum lactate, basic aluminum halides such as $Al_2(OH)_5Cl$, aluminum bromide and the several water, alcohol or glycine complexes thereof.

The amount of astringent that is dissolved in water to form the compositions may vary widely; however, certain practical limitations exist. On the one hand an efficacious antiperspirant composition would contain sufficient astringent to provide sweat reduction, although compositions containing less astringent can be useful in personal care compositions. Preferably, the antiperspirant composition comprises approximately 10–25 weight percent astringent. On the other hand, it is desirable to maximize the amount of water in the antiperspirant formulation without negating utility, for obvious economic reasons. Depending on the particular astringent that is used, the composition may vary in concentration from as little as one part by weight astringent per three parts by weight water up to a saturated aqueous solution of the astringent.

Other ingredients that can be present in the antiperspirant compositions include dimethicone or dimethiconol fluids. Dimethicone is generally known to be a methyl-stopped polydimethylsiloxane polymer; and dimethiconol is an OH-stopped polydimethylsiloxane polymer. These ingredients provide better aesthetic feel. The amounts of these optional ingredients is from about 0 parts to about 8 parts based on total parts of the composition.

Surfactants are optionally added to the compositions of the present invention. These include any hydrophilic emulsifier with an HLB greater than 8. The amount of surfactant is generally from about 0 parts to about 2 parts based on 100 parts of the total composition. However, it is recognized that one skilled in the art would realize this amount is adjusted based upon the required HLB of the system.

The compositions of this invention may further comprise other non-essential components which are used in the cosmetic and personal care art. Examples of such components include colorants; perfumes; viscosity control additives, such as solvents or thickening agents for the continuous phase; and non-volatile organopolysiloxanes, such as ester silicone copolymers, alkyl silicone copolymers, methyl phenyl silicone, vinyl silicone fluids etc. Those skilled in the art would recognize other ingredients can be added.

In one embodiment of the invention, the oil phase ingredients, such as the silicone terpolymer, the volatile liquids, the solubilizing agent, and dimethicone if present, are mixed by any method known to the art. The water-phase ingredients are also mixed in a separate vessel. The refractive index (RI) of each phase is measured separately. Adjustments are made so the two phases are preferably within 0.00010 units of each other to ensure optical clarity of the final mixture. The two phases are combined as a water-in-oil emulsion by slowly pouring the water phase into the oil phase while stirring with a moderate shear mixer. The blend is then processed at high shear on a homogenizer or other suitable equipment to reduce particle size to enhance clarity and stability of the emulsion.

Small particle size of the composition is important for maintaining the clarity and stability of the AP compositions. By small it is meant a particle size of less than about 10 microns, preferably less than about 5 microns, and still more preferably less than about 3 microns.

DESCRIPTION OF THE PREFERRED EMBODIMENTS

The following examples illustrate the present invention. They are not to be construed to limit the scope of the claims in any manner whatsoever.

EXAMPLE 1

Preparation of batch

The water-in-oil emulsion clear gel antiperspirant was prepared in 400 g batches. Aluminum chlorohydrate or aluminum-zirconium tetrachlorohydrex glycine (ZAG) were used as the AP active ingredient.

The oil phase ingredients were weighed and added to a 600 mL stainless steel beaker in the order listed in Table 1.

The mixture was hand stirred with a spatula. The water phase ingredients, with the exception of the last part water, were measured and added to a separate beaker and stirred until homogenous. A few drops of each of the phases were removed and the refractive index (R.I.) was determined. The last ~1 part of water was added by small increments to match the water phase R.I. to the oil phase R.I. within <0.00010 units. This step was repeated until the desired R.I. match was achieved.

The oil phase was mixed under moderate shear conditions. The water phase was gradually poured into the oil phase without permitting phase reversal. After all of the water phase ingredients were added, the mixture was stirred for approximately 10 minutes. The mixture was then place into a high shear homogenizer and the speed was slowly increased and the mixture was agitated until a gel was formed. The material was allowed to deaerate at room conditions.

The final product was evaluated for clarity and R.I. was determined. The product was also applied to skin to evaluate feel and non-whitening properties.

R.I. was measured on a Bausch & Lomb Refractometer to 0.00010 unit at 25°±0.5° C.

Clarity was measured according to visual comparison through a 1" thick film. Skin feel was measured using a subjective comparison, and non-whitening properties were also determined by a subjective comparison. The samples all formed non-tacky, non-whitening films on the skin and appeared clear in typical consumer applicator containers measuring 1 inch in thickness.

EXAMPLE 2

Comparative Example U.S. Pat. No. 4,980,156

A sample representative of the U.S. Pat. No. 4,980,156 (Raleigh et al.) was prepared by the procedures described in that patent. Additionally, the refractive index values of the separate phases and of the final emulsion was measured. However, as in Raleigh et al., no steps were taken to match the RI values of the separate phases.

The results can be seen in Table 1 (formulation V).

TABLE 1

| | CLEAR GEL ANTIPERSPIRANT FORMULATIONS | | | | |
| --- | --- | --- | --- | --- | --- |
| FORMULATION | I | II | III | IV | EXAMPLE 2 V |
| Part A Oil Phase | | | | | |
| SF1204* Volatile silicones | 17.0 | 17.0 | 16.0 | 16.0 | 23.0 |
| Isopropyl palmitate | — | — | 1.0 | 1.0 | — |
| 218-1138* Silicone terpolymer | 3.0 | 3.0 | 3.0 | 3.5 | 3.0 |
| SF96-20* Dimethicone | 4.0 | 4.0 | 4.0 | 3.0 | — |
| SF96-50* Dimethicone | — | — | — | 1.0 | — |
| Part B Water Phase | | | | | |
| Water | 14.3 | 18.8 | 13.3 | 17.2 | 33.6 |
| Propylene glycol | 10.0 | 10.0 | 10.0 | 10.0 | — |
| Polysorbate-80 Surfactant | 0.66 | 0.66 | 0.66 | 0.77 | 0.4 |
| 50% Aluminum chlorohydrate (aq) | 40.0 | — | 40.0 | — | 40.0 |

TABLE 1-continued

CLEAR GEL ANTIPERSPIRANT FORMULATIONS

| FORMULATION | I | II | III | IV | EXAMPLE 2 V |
|---|---|---|---|---|---|
| 50% ZAG(ag) | — | 40.0 | — | 40.0 | — |
| 70% Sorbitol (ag) | 10.0 | 5.5 | 11.0 | 7.15 | — |
| Water (match Part A R.I.) | ~1.0 | ~1.0 | ~1.0 | ~1.0 | — |
| Measurements | | | | | |
| Part A R.I. | 1.3996 | 1.3996 | 1.4018 | 1.4023 | 1.3950 |
| Part B R.I. | 1.3990 | 1.3990 | 1.4020 | 1.4025 | 1.3740 |
| Final R.I. | 1.4010 | 1.4000 | 1.4032 | 1.4034 | 1.3850 |
| Appearance | transparent | transparent | transparent | transparent | opaque |

*Supplied by GE Silicones
All values listed are in parts per 100 based upon the total number of parts of the formulation.

The above mentioned patents and publications are hereby incorporated by reference.

Many variations of the present invention will suggest themselves to those skilled in this art in light of the above detailed description. All such obvious modifications are within the full intended scope of the appended claims.

We claim:

1. A transparent antiperspirant composition consisting essentially of:

equal or less than 3.5% of a hydrocarbon—modified polydiorganosiloxane polyoxyalkylene copolymer having the general formula:

$$MD_xD'_yD''_zM$$

wherein

D is $(CH_3)_2SiO_{2/2}$;
D' is $(CH_3)R'SiO_{2/2}$ where R' is an alkyl group having from about 6 to about 30 carbon atoms;
D" is $(CH_3)R^2SiO_{2/2}$ where $R^2$ is a polyoxyalkylene ether segment of the formula $$-(R^4)_p-(OR^3)_n-OR^5$$

wherein each individual $R^3$ is an alkylene radical having 2 to 6 carbon atoms, $R^4$ is an unsubstituted alkylene radical having 2 to 20 carbons, and $R^5$ is hydrogen, or an unsubstituted hydrocarbon radical of from 1 to about 12 carbon atoms, and n has an average value from about 5 to about 20, p has a value of zero or 1, M is $(CH_3)_2R^6SiO_{2/2}$, where $R^6$ is an alkyl group having from 1 to 30 carbon atoms or $R^2$;
x has an average value of from about 10 to about 400;
y has an average value of from 1 to about 200;
z has an average value of from 1 to about 100; and
x+y+z has an average value of from about 12 to about 400; and effective amounts of
a volatile liquid having a boiling point below about 250° C.;
a solubilizing agent selected from the group consisting of isopropyl palmitate, isopropyl myristate, lauryl alcohol and silicone fluids having a viscosity below 50 centistokes at 25° C.; water;
a refractive index adjuster whereby the difference in refractive index between an oil phase and an aqueous phase is less than 0.0020 refractive index units; and
an astringent salt selected from the group consisting of the salts, water, alcohol and glycerine complexes of aluminum, hafnium and zirconium.

2. An antiperspirant composition of claim 1, wherein said composition forms a non-whitening, clear emulsion.

3. An antiperspirant composition as defined in claim 2 wherein D' is $(CH_3)R'SiO_{2/2}$, where R' is an alkyl group having from about 8 to about 18 carbon atoms.

4. An antiperspirant composition as defined in claim 3 wherein D" is $(CH_3)R^2SiO_{2/2}$ where $R^2$ is a polyoxyalkylene ether segment of the formula $$-(R^4)_p-(OR^3)_n-OR^5$$

wherein each individual $R^3$ is an unsubstituted alkylene radical having from about 2 to about 4 carbon atoms, $R^4$ is an unsubstituted alkylene radical having from about 2 to about 6 carbon atoms, and $R^5$ is hydrogen or a hyrocarbon radical having from 1 to about 4 carbon atoms, and n has an average value from about 10 to about 15.

5. An antiperspirant composition as defined in claim 4 wherein M is $(CH_3)_2R^6SiO_{2/2}$, where $R^6$ is an alkyl group having from 1 to about 6 carbon atoms.

6. An antiperspirant composition as defined in claim 3 wherein said $R^3$ is 2; $R^4$ is 3; n is 12; and p is 1.

7. An antiperspirant composition as defined in claim 6 wherein M is $(CH_3)_2R^6SiO_{2/2}$, where $R^6$ is an alkyl group having 1 carbon atoms.

8. An antiperspirant composition as defined in claim 7 wherein said composition forms a non-whitening, clear gel.

9. An antiperspirant composition as defined in claim 1 wherein the volatile liquid is volatile silicone.

10. An antiperspirant composition as defined in claim 9, wherein the volatile silicone is cyclic silicone and present in an amount of from 5–40 parts based upon the total composition.

11. An antiperspirant composition as defined in claim 1, wherein the solubilizing agent is isopropyl palmitate, isopropyl myristate, or mixtures thereof and is present in an amount of from about 0.1 to about 20 parts based upon the total weight of the composition.

12. An antiperspirant composition as defined in claim 8, wherein the refractive index adjuster is a glycol or polysaccharide.

13. An antiperspirant composition as defined in claim 12 wherein the refractive index adjuster is a mixture of propylene glycol and sorbitol.

14. An antiperspirant composition as defined in claim 1, wherein said composition forms a non-whitening, clear emulsion.

15. An antiperspirant formed from the composition as defined in claim 1, wherein the particle size is small enough to provide a transparent or substantially transparent emulsion when viewed through a 1 inch thick container.

16. An antiperspirant composition as defined in claim 14 wherein $R^3$ is 2; $R^4$ is 3; n is 12; and p is 1.

17. An antiperspirant composition as defined in claim 16 wherein M is $(CH_3)_2R^6SiO_{2/2}$, where $R^6$ is an alkyl group having 1 carbon atom.

18. An antiperspirant emulsion composition prepared from an oil phase and a water phase having the composition as defined in claim 17, wherein the refractive indices of the phases are matched within about 0.00010 refractive index units at 25°±0.5° C.

19. An antiperspirant composition as defined in claim 18, wherein the volatile silicone is cyclic silicone and is present in amount of from 15 to about 20 parts based upon the total composition.

20. An antiperspirant composition as defined in claim 1, wherein the particle size is small enough to provide a transparent or substantially transparent emulsion when viewed through a 1 inch thick container.

21. An antiperspirant composition as defined in claim 17, wherein said composition form a non-whitening, clear gel.

* * * * *

REEXAMINATION CERTIFICATE (4229th)

United States Patent
Powell et al.

[11] B1 5,456,906
[45] Certificate Issued  Dec. 5, 2000

[54] ANTIPERSPIRANT COMPOSITIONS

[75] Inventors: Virginia V. Powell, East Nassau; Stanley J. Stoklosa, Clifton Park; Raymond J. Thimineur, Scotia, all of N.Y.

[73] Assignee: General Electric Company, Schnectady, N.Y.

Reexamination Request:
No. 90/005,151, Oct. 19, 1998

Reexamination Certificate for:
Patent No.: 5,456,906
Issued: Oct. 10, 1995
Appl. No.: 08/154,246
Filed: Nov. 17, 1993

[51] Int. Cl.[7] ............................. A61K 7/34; A61K 7/38; A61K 9/10

[52] U.S. Cl. .................. 424/66; 424/65; 424/68; 424/400; 424/401; 514/938; 514/944; 514/DIG. 5

[58] Field of Search .................. 424/65, 66, 68, 424/400, 401; 514/938, 944, DIG. 5

[56] References Cited

U.S. PATENT DOCUMENTS

4,980,156  12/1990  Raleigh et al. ................. 424/66

FOREIGN PATENT DOCUMENTS

WO 92/05767  4/1992  European Pat. Off. ......... A61K 7/34

*Primary Examiner*—Shelley Dodson

[57] ABSTRACT

The present invention provides novel water-in-oil antiperspirant compositions which are transparent or substantially transparent, leave no white residue, and have a non-tacky feel.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 10–28:

Refractive Index (RI) adjusters are contemplated for use in the present invention. These RI adjusters include compounds for raising the RI value of the water-phase of the compositions as well as compounds [RI of the phases.useful] for [lowing] *lowering* the RI of the oil-phase of the compositions. Such compounds include, propylene glycol, glycerin, sorbitol, silicone polyether copolymer or any water soluble-polar-type material. Water soluble inorganic salts, such as sodium chloride can also be used to adjust the water phase. In addition to the water based RI adjusters, oil phase adjusters such as esters, hydrocarbon oils such as mineral oil, long-chain alcohols or other mixtures can be used. The amount of RI adjuster used varies depending on the RI of the water- and oil- phases, and is generally present in an amount sufficient to adjust the RI of the water phase and oil phase to obtain optical clarity. This means the RI of the two phases are within at least about 0.0020 RI units of each other, and preferably within about 0.00010 units and most preferably there is no difference in *the RI of the two phases.*

AS A RESULT OF REEXAMINATION, IT HAS BEEN DETERMINED THAT:

The patentability of claims 1–21 is confirmed.

* * * * *